United States Patent [19]

Arai et al.

[11] Patent Number: 4,578,245

[45] Date of Patent: Mar. 25, 1986

[54] MULTILAYER ANALYTICAL ELEMENT

[75] Inventors: Fuminori Arai, Asaka; Yoshio Inagaki, Minami-ashigara; Masao Kitajima, Asaka, all of Japan

[73] Assignee: Fuji Photo Film Co., Ltd., Kanagawa, Japan

[21] Appl. No.: 534,085

[22] Filed: Sep. 20, 1983

[30] Foreign Application Priority Data

Sep. 22, 1982 [JP] Japan ................... 57-165233

[51] Int. Cl.$^4$ ............ G01N 21/78; G01N 31/22; C12Q 1/00
[52] U.S. Cl. .................... 422/56; 422/60; 435/11; 435/14
[58] Field of Search ............ 435/11, 14; 422/56, 422/60

[56] References Cited

U.S. PATENT DOCUMENTS

| | | | |
|---|---|---|---|
| 3,983,005 | 9/1976 | Goodhue et al. | 435/11 |
| 3,992,158 | 11/1976 | Przybylowicz et al. | 422/57 |
| 4,292,272 | 9/1981 | Kitajima et al. | 422/56 |
| 4,384,042 | 5/1983 | Miike et al. | 435/11 |

*Primary Examiner*—Christine M. Nucker
*Attorney, Agent, or Firm*—Toren, McGeady, Stanger, Goldberg & Kiel

[57] ABSTRACT

A multilayer analytical element comprising a water-impermeable, light-transmissive support, a reagent layer containing a color forming reagent composition for detection of hydrogen peroxide including at least combination of a chromogen and a coupler (a color indicator composition), and peroxidase, which produces a detectable change in the presence of peroxidase and hydrogen peroxide, and a porous spreading layer, which are superposed in this order, in which said chromogen is a 1,2,3-tri-substituted compound of 4-amino-3-pyrazolin-5-one having solubility in water at 25° C. of lower than that of 4-amino-2,3-dimethyl-1-phenyl-3-pyrazolin-5-one.

7 Claims, 3 Drawing Figures

MULTILAYER ANALYTICAL ELEMENT

BACKGROUND OF THE INVENTION

1. Field of the Invention

This invention relates to a multilayer analytical element. More particularly, this invention relates to an improvement of a multilayer analytical element containing a color indicator system for detection of hydrogen peroxide which is appropriately employable in quantitative analysis of hydrogen peroxide in a liquid sample, or in quantitative analysis of a specific component through quantitative determination of the amount of hydrogen peroxide produced upon contact of the specific component with an oxidase enzyme system.

2. Description of Prior Arts

A quantitative analysis of a specific component (referred to herein as "analyte") based on quantitative determination of the amount of $H_2O_2$ produced by an oxidation reaction between the analyte or a reaction product of the analyte and oxidase, by means of an appropriate determination procedure has recently become more important. The reason is that the quantitative determination of $H_2O_2$ can be done accurately and reliably, for instance, by colorimetric determination of a colored product formed by the action of $H_2O_2$ in the presence of peroxidase.

As for the colorimetric determination method based on the above-mentioned principle, there is known a method using a reagent system proposed by P. Trinder (Ann. Clin. Biochem., 6, 24–27 (1969)). This method involves: producing $H_2O_2$ by a reaction between an analyte and oxidase; causing an oxidative coupling reaction between 4-aminoantipyrine (or an analogue thereof) and a phenol (or a naphthol) in the presence of produced $H_2O_2$ and peroxidase to produce a colored product; and quantitatively determining the so produced colored product. This reaction system is advantageous because the same detection system is employable regardless of varying the kind of oxidase. Accordingly, this reaction system has been studied for application in detection of various analytes. Examples of oxidases particularly important in the art of clinical chemical tests include glucose oxidase, cholesterol oxidase, uricase, glycerol oxidase, and phosphoglucose oxidase, etc.

An analytical element employing said oxidase and a detection system for the produced $H_2O_2$ in the form of an integral multilayer analytical element, or a strip (such as a filter paper strip) impregnated with these reagents is widely employed for clinical tests. These analytical elements comprise a composition containing reagents directly participating in the detection of an analyte which is impregnated in a filter paper strip or the like, or coated over a filmy support.

The integral multilayer analytical element can be in a variety of constitutions, and different functional layers can be incorporated into the element under lamination as need arises. Examples of known functional layers include: a spreading layer for uniform spreading of a liquid sample (U.S. Pat. No. 3,992,158, GB No. 1 440 464, and U.S. Pat. No. 4,292,272); a light-shielding layer providing a light-scattering white surface for reflective measurement, as well as serving for optically separating the colored product produced upon the reaction from colored components contained within the upper layer (U.S. Pat. No. 3,992,158, GB No. 1,440,464, and U.S. Pat. Nos. 4,042,335, 4,255,384, and 4,292,274, etc.); a barrier layer for selective diffusion of component, product, etc. (U.S. Pat. No. Re. 30,267) or a liquid-blocking air barrier layer for the same purpose (Japanese Patent Provisional Publication No. 58(1983)-77660, and GB 2 114 737A); a detection layer for efficient detection by mordanting the colored product (U.S. Pat. Nos. 4,042,335 and 4,144,306); a migration inhibiting layer for preventing diffusion of the colored product into other layers (U.S. Pat. No. 4,166,093); and an adhesive layer for improvement of adhesion between the incorporated layers (U.S. Pat. No. 4,292,272, etc.).

As a result of the study of the present inventor, it has been noted that a calibration curve prepared for quantitative analysis of glucose or cholesterol using a multilayer analytical element containing in its reagent layer a color-forming reagent composition for detection of $H_2O_2$ including glucose oxidase or a combination of cholesterol esterase and cholesterol oxidase, peroxidase, 4-aminoantipyrine, and 1,7-dihydroxynaphthalene shows a relatively gentle slope ($\gamma$), and particularly gentle in a high concentration region where a liquid sample containing a great amount of glucose or cholesterol is calibrated. This means that such a analytical element gives poor accuracy in the quantitative analysis, as well as narrow measurable range.

SUMMARY OF THE INVENTION

The present inventors have studied the above-mentioned problem and discovered that employment of a 1,2,3-tri-substituted compound of 4-amino-3-pyrazolin-5-one which is analogous to 4-aminoantipyrine (i.e. 4-amino-2,3-dimethyl-1-phenyl-3-pyrazolin-5-one) but has lower solubility in water than that of the 4-aminoantipyrine in the reagent layer of the multilayer analytical element in place of the 4-aminoantipyrine effectively eliminates the above-mentioned problem. This 1,2,3-tri-substituted compound having poor solubility has been not employed for the instant object in a wet process (conducted in an aqueous solution) for quantitative analysis of glucose or cholesterol, because in the wet process it gives color formation of poor optical density and accordingly is low in the sensitivity.

Accordingly, a primary object of the present invention is to provide an improved multilayer analytical element containing a color-forming reagent composition for detection of $H_2O_2$ in a reagent layer, in which a calibration curve prepared in the analytical process using said element has a steep slope ($\gamma$) and said steep slope is maintained even in a high analyte-concentration region, whereby the measurable range is broadened, the sensitivity is enhanced, and the quantitative accuracy is improved.

Another object of the invention is to provide an improved multilayer analytical element containing a color-forming reagent composition including a combination of a chromogen and a coupler, and peroxidase for detection of $H_2O_2$ in a reagent layer, in which a calibration curve prepared in the analytical process using said element has a steep slope ($\gamma$) and said steep slope is maintained even in a high analyte-concentration region, whereby the measurable range is broadened, the sensitivity is enhanced, and the quantitative accuracy is improved.

A further object of the invention is to provide an improved multilayer analytical element containing a color-forming reagent composition including a combination of a chromogen and a coupler, oxidase and peroxidase for detection of $H_2O_2$ in a reagent layer, in which a calibration curve prepared in the analytical process using said element has a steep slope ($\gamma$) and said steep slope is maintained even in a high analyte-concentration region, whereby the measurable range is broadened, the sensitivity is enhanced, and the quantitative accuracy is improved, and which enable to carry out the analytical process within a short period of time.

The present invention provides:

(1) A multilayer analytical element comprising a water-impermeable, light-transmissive support, a reagent layer containing a color forming reagent composition for detection of hydrogen peroxide including at least a combination of a chromogen and a coupler (a color indicator composition) and peroxidase, which produces a detectable change in the presence of peroxidase and hydrogen peroxide, and a porous spreading layer, which are superposed in this order,
in which said chromogen is a 1,2,3-tri-substituted compound of 4-amino-3-pyrazolin-5-one having solubility in water at 25° C. of lower than that of 4-amino-2,3-dimethyl-1-phenyl-3-pyrazolin-5-one (free amine).

(2) The multilayer analytical element as described in the above (1), in which said coupler is a compound capable of forming a dye together with the 1,2,3-tri-substituted compound of 4-amino-3-pyrazolin-5-one through oxidative coupling reaction in the presence of peroxidase and hydrogen peroxide.

(3) The multilayer analytical element as described in the above (1) or (2), in which said reagent layer contains said 1,2,3-tri-substituted compound of 4-amino-3-pyrazolin-5-one and said coupler and peroxidase.

(4) The multilayer analytical element as described in any one of the above (1) through (3), in which oxidase is contained in said reagent layer or any other layer.

(5) The multilayer analytical element as described in the above (4), in which said oxidase is selected from the group consisting of glucose oxidase, cholesterol oxidase, pyruvate oxidase, uricase, ascorbate oxidase, lactate oxidase, and glycerol oxidase.

(6) The multilayer analytical element as described in the above (4), in which said oxidase is glucose oxidase.

(7) The multilayer analytical element as described in the above (4), in which said oxidase is cholesterol oxidase.

DESCRIPTION OF PREFERRED EMBODIMENTS

Figure 1:
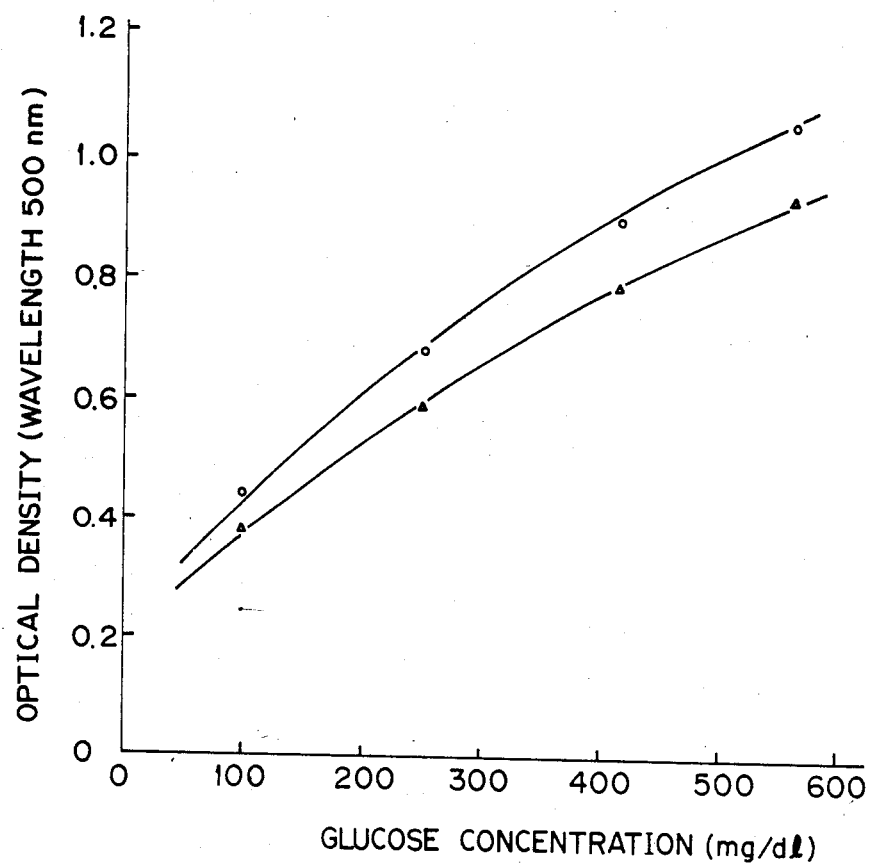
FIG. 1 through FIG. 3 are calibration curves indicating relationships between glucose content (concentration) in liquid samples and optical density of formed color which were prepared in the use of multilayer analytical elements according to the present invention as well as multilayer analytical elements produced for comparison purpose. In these figures, a curve having circlar marks and a curve having triangular marks represent calibration curves of the multilayer analytical element (film) of the invention and that of the comparison example. The quantitative analysis was carried out on human whole blood samples and human plasma samples containing different amounts of glucose. The measurement was made through reflective measurement procedure.

There is no specific limitation on the water-impermeable, light-transmissive support comprised in the multilayer analytical element of the present invention, so far as it allows transmission of applied electromagnetic waves in the wavelength range of approx. 200 nm to approx. 900 nm, such as ultraviolet rays, near-ultraviolet rays, visible rays and near-infrared rays at a ratio of not less than approx. 40%, preferably not less than approx. 65%, permits substantially no permeation of water thereinto, and is substantially chemically inert to a polymer binder and other materials comprised in the hereinafter-described reagent layers and/or under-coating layer to be superposed on the support. Examples of the support include a transparent sheet or film made of a polymer such as polyethylene terephthalate, polycarbonate of bisphenol A, polymethyl methacrylate, polystyrene, cellulose esters (e.g., cellulose diacetate, cellulose triacetate, and cellulose acetate propionate) and a transparent glass plate. The thickness of the support generally ranges from approx. 50 $\mu$m to approx. 2 mm, preferably from approx. 70 $\mu$m to approx. 0.5 mm.

On a surface of the support can be provided a known under-coating layer for facilitating adhesion of a reagent layer or one of other functional layers against the support so as to form an integrated structure. For the same purpose, the surface of the support can be modified by a known chemical processing such as acid processing or alkaline processing, or a known physical processing such as corona discharge processing, glow discharge processing, ultraviolet rays irradiation processing or flame processing.

The reagent layer comprised in the multilayer analytical element of the present invention is a reagent layer which comprises a hydrophilic polymer binder and a color-forming reagent composition for detection of hydrogen peroxide (referred to hereinafter as "color-forming reagent for $H_2O_2$") being dispersed or dissolved in the matrix of the former polymer binder.

The color-forming reagent for $H_2O_2$ is a color-forming reagent composition comprising peroxidase and a combinatioin of chromogen and coupler (a color indicator composition) and peroxidase, which produces a detectable change (generally, change of color density, or change of hue) in the presence of peroxidase and hydrogen peroxide.

The chromogen employed in the color-forming reagent of the present invention is a 1,2,3-tri-substituted compound of 4-amino-3-pyrazolin-5-one (hereinafter referred to as "tri-substituted-4-amino-3-pyrazolin-5-one) having lower solubility in water at 25° C. than that of 4-amino-2,3-dimethyl-1-phenyl-3-pyrazolin-5-one (i.e. 4-aminoantipyrine), in which the solubility is determined in the form of a free amine for both compounds. More in detail, the tri-substituted-4-amino-3-pyrazolin-5-one employed in the invention has solubility of not higher than approx. 5 g., preferably not higher than 0.2 g., in 10 ml. of water (purified water almost as pure as distilled water) at 25° C. in the free amine form. A compound satisfying the above-defined conditions on the solubility in water can be a tri-substituted-4-amino-3-pyrazolin-5-one having a molecular weight at least 10 higher than the molecular weight of 4-aminoantipyrine (203.2). In most cases, the tri-substituted-4-amino-3-pyrazolin-5-one having a molecular weight at least 10 higher than that of the 4-aminoantipyrine provides a satisfactory result.

Examples of the tri-substituted-4-amino-3-pyrazolin-5-one employable in the present invention include compounds represented by the following formulae (1) to (4), in which the numbers attached to the pyrazoline nucleus indicate the position numbers.

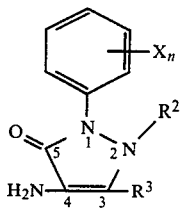

(1)

In the formula (1), X is a halogen atom such as chlorine, bromine or iodine; n is 1, 2 or 3; and each of $R^2$ and $R^3$ may be the same or different and is an alkyl or phenyl group; in which X can be attached to an optional position and, in the case that n is 2 or 3, these X can be the same or different halogen atoms.

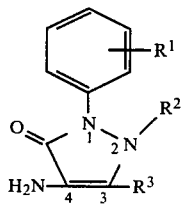

(2)

In the formula (2), $R^1$ is a hydrogen atom, or a lower alkyl or alkoxy group attached to an optional position; and each of $R^2$ and $R^3$ may be the same or different and is an alkyl or phenyl group; in which the case where $R^1$ is the hydrogen atom and $R^2$ and $R^3$ are both methyl groups is excluded.

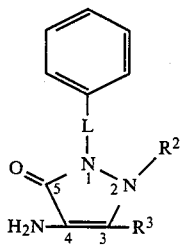

(3)

In the formula (3), L is a methylene or ethylene group; and each of $R^2$ and $R^3$ may be the same or different and is an alkyl or phenyl group.

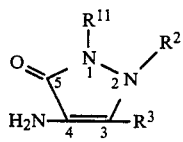

(4)

In the formula (4), $R^{11}$ is an alkyl group; and each of $R^2$ and $R^3$ may be the same or different and is an alkyl or phenyl group; in which the total number of carbon atoms contained in $R^{11}$, $R^2$ and $R^3$ is not less than 9.

Examples of the halogen-substituted phenyl group attached to the 1-position of the tri-substituted-4-amino-3-pyrazolin-5-one represented by the formula (1) include 2-chlorophenyl, 3-chlorophenyl, 4-chlorophenyl, 2,5-dichlorophenyl, 3,4-dichlorophenyl, 3,5-dichlorophenyl, 2,4,6-trichlorophenyl, 4-bromophenyl, and 4-iodophenyl group.

In the formula (2), the lower alkyl group for $R^1$ is a straight or branched chain alkyl group having 1–5 carbon atoms. Examples of the lower alkyl group include methyl, ethyl, propyl, butyl, isopropyl and isoamyl groups. The lower alkoxy group for $R^1$ contains as its alkyl portion a straight or branched chain alkyl group having 1–5 carbon atoms. Examples of the lower alkoxy group include methoxy, ethoxy, propoxy, butoxy and isopropoxy groups. The $R^1$ is preferably attached to the 4-position. Preferred examples of the $R^1$-substituted phenyl group include 4-methylphenyl, 4-ethylphenyl, 4-methoxyphenyl and 4-ethoxyphenyl groups.

In the formulae (1) to (4), the alkyl group for $R^2$ is a straight or branched chain alkyl group having 1–18 carbon atoms. Examples of the alkyl group include methyl, ethyl, propyl, butyl, pentyl, hexyl, octyl, nonyl, dodecyl, tridecyl, hexadecyl, octadecyl, isopropyl, isobutyl and isoamyl groups. The alkyl group for $R^3$ is a straight or branched chain alkyl group having 1–18 carbon atoms, or a cycloalkyl group having 3–18 carbon atoms. Examples of the alkyl group include cyclopropyl, cyclopentyl, cyclohexyl, cyclohexylmethyl, 2-cyclohexylethyl, 4-methylcyclohexyl and 4-ethylcyclohexyl groups in addition to the alkyl groups as exemplified above for $R^2$.

In the formula (4), the alkyl group for $R^{11}$ is a straight or branched chain alkyl group having 1–18 carbon atoms. Examples of the alkyl group include those as exemplified above for $R^2$.

In the formula (3), L is preferably the methylene group.

Any of the tri-substituted-4-amino-3-pyrazolin-5-ones represented by the formulae (1) to (4) can be in the form of an acid addition salt (i.e. 4-ammonio-3-pyrazolin-5-one) in which an acid is attached to the amino group in the 4-position. Examples of the acid employable for the formation of the acid addition salt include inorganic acids such as hydrochloric acid, hydrobromic acid, hydroiodic acid, perchloric acid and sulfuric acid, and organic acids such as formic acid, acetic acid, propionic acid, oxalic acid, glutaric acid, 3,3-dimethylglutaric acid, malic acid, tartaric acid and p-toluenesulfonic acid. A preferable acid addition salt is a hydrochloric acid addition salt.

Among the tri-substituted-4-amino-3-pyrazolin-5-ones represented by the formulae (1) to (4) and their acid addition salts, compounds having in any of the 1-, 2-, and 3-positions a substituent containing at least one benzene nucleus (phenyl group, or a substituted phenyl or benzyl group) are preferred.

Representative examples of the tri-substituted-4-amino-3-pyrazolin-5-ones represented by the formulae (1) to (4) are set forth in Table 1, in which 19 compounds of the compound (1) through (19) and their acid addition salts are preferred. Most preferred are the compounds of (6), (7), and (18) and their monohydrochlorides.

TABLE 1

| Compound | Substituents | | | M.p., Reference, or |
| --- | --- | --- | --- | --- |
| | 1-position | 2-position | 3-position | CA Registry No. |
| (1) | 3-chloro- | methyl | methyl | monohydrochloride |

TABLE 1-continued

| Com-pound | Substituents 1-position | 2-position | 3-position | M.p., Reference, or CA Registry No. |
|---|---|---|---|---|
| | phenyl | | | m.p. 185° C. (dec.) JPPP 58(1983)-124771 |
| (2) | 4-chlorophenyl | methyl | methyl | m.p. 104.5–106° C.* |
| (3) | 2,5-dichlorophenyl | methyl | methyl | m.p. 120–125° C. (crude)* |
| (4) | 3,4-dichlorophenyl | methyl | methyl | m.p. 125–130° C. (crude)* |
| (5) | 3,5-dichlorophenyl | methyl | methyl | m.p. 128–133° C. (crude)* |
| (6) | 2,4,6-trichlorophenyl | methyl | methyl | m.p. 146–148° C. (crystallized from isopropyl alcohol) JPPP 58(1983)-124771 monohydrochloride m.p. 236° C. (dec.) |
| (7) | 2,4,6-trichlorophenyl | methyl | methyl | m.p. 150–152° C. (crystallized from isopropyl alcohol) JPPP 58(1983)-124771 |
| (8) | 4-bromophenyl | methyl | methyl | m.p. 133° C. CA 52,6325h |
| (9) | 4-iodophenyl | methyl | methyl | m.p. 147–148° C. (alc.)[24664-30-0] |
| (10) | p-tolyl | methyl | methyl | [67019-57-2] monohydrochloride [(56430-10-5)] CA 83,97119v |
| (11) | 4-ethoxyphenyl | methyl | methyl | m.p. 132–133° C. CA 52,6325h |
| (12) | 4-propoxyphenyl | methyl | methyl | m.p. 99–100° C. CA 50,989f |
| (13) | 4-isopropoxyphenyl | methyl | methyl | m.p. 105–107° C. Ger. Pat. 897,406 (CA 52,10207f) |
| (14) | phenyl | methyl | cyclopropyl | m.p. 125° C. (from benzene-ligroin) U.S. Pat. No. 2,731,473 (CA 50,10792g) |
| (15) | phenyl | ethyl | ethyl | m.p. 82–84° C. CA 52,172364 |
| (16) | phenyl | hexadecyl | methyl | 124° C.(crystallized from $C_6H_{12}$) Belg. Pat. 563,474 (CA 54,16241g) |
| (17) | phenyl | phenyl | methyl | Belg. Pat. 563,474 (CA 54,16241g) |
| (18) | phenyl | methyl | phenyl | [52744-73-7] CA 81,3822c |
| (19) | benzyl | methyl | methyl | m.p. 54° C., Brit. Pat. 779,703(CA 52, 11954c), m.p. 74° C. (crystallized from ethyl acetate) hydrochloride, m.p. 197° C. (crystallized from ethyl alcohol) CA 50,64371g |
| (20) | methyl | methyl | nonyl | monohydrochloride U.S. Pat. No. 3,079,256 (CA 59,12961f-12962b) |
| (21) | methyl | methyl | tridecyl | U.S. Pat. No. 3,079,256 (CA 59,12961f-12962b) |
| ($C_1$) | phenyl | methyl | methyl | [83-07-8] monohydrochloride [22198-72-7] |
| ($C_2$) | methyl | methyl | phenyl | Ger. Pat. 927,992 (CA 52,20200b) |

The coupler included in the color-forming reagent for $H_2O_2$ according to the invention is a compound which forms a dye in conjunction with the chromogen through oxidative coupling reaction in the presence of peroxidase and hydrogen peroxide.

Examples of the coupler include phenol, naphthol, phenol derivatives having substituent such as halogen (chlorine, bromine, etc.), alkyl, alkoxy, phenyl, phenoxy, nitro, or hydroxyl group, and naphthol derivatives having substituents mentioned as above, as described in FR 2 185 289 (U.S. Pat. No. 3,886,045) and U.S. Pat. No. 3,886,045, Clinical Chemistry, 24(8), 1335–1342(1978), and "The Theory of the Photographic Process" edited by C. E. K. Mees and T. H. James (Third Edition, Macmillan Co., 1968), pp. 387–396; phenol derivatives and naphthol derivatives having a ballasting group, as described in the above-mentioned "The Theory of the Photographic Process", pp. 387–396, and Japanese Patent Provisional Publication No. 57(1982)-94655; hydroxyquinolines having an alkyl group or hydroxyquinoline having no other groups, as described in FR No. 2 185 289 (U.S. Pat. No. 3,886,045); and active methylene-containing straight chain compounds and active methylene-containing cyclic compounds, as described in the above-mentioned "The Theory of the Photographic Process", pp. 387–396, etc.

Among these couplers, phenol and phenol derivatives having the following formula (6), as well as naphthol and naphthol derivatives having the following formula (7) are preferred.

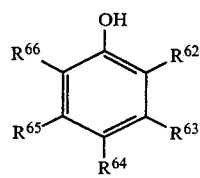
(6)

In the formula (6), each of $R^{62}$ through $R^{66}$ is a hydrogen atom, a hydroxyl, alkyl, alkoxy, phenyl, benzyl, phenethyl or nitro group, or a halogen atom (chlorine, bromine or iodine), in which at least two of $R^{62}$ through $R^{66}$ are hydrogen atoms.

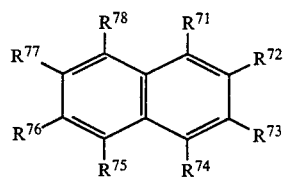
(7)

In the formula (7), each of $R^{71}$ through $R^{78}$ is a hydrogen atom, a hydroxyl, alkyl, alkoxy, phenyl, benzyl, phenethyl or nitro group, or a halogen atom (chlorine, bromine or iodine), in which at least one of $R^{71}$ through $R^{78}$ is a hydroxyl group, at least four of $R^{71}$ through $R^{78}$ are hydrogen atoms.

The alkyl group for $R^{62}$ through $R^{66}$ in the formula (6), as well as for $R^{71}$ through $R^{78}$ in the formula (7), can be a straight or branched chain alkyl having 1–18 carbon atoms or a cycloalkyl group having 3–18 carbon atoms. Examples of the alkyl group include methyl, ethyl, propyl, butyl, pentyl, hexyl, isopropyl, isobutyl, isoamyl, cyclopropyl, cyclopentyl and cyclohexyl groups.

The alkoxy group for $R^{62}$ through $R^{66}$, as well as for $R^{71}$ through $R^{78}$, can be an alkoxy group containing a straight or branched chain alkyl having 1–18 carbon atoms or a cycloalkyl group having 3–18 carbon atoms. Examples of the alkoxy group include methoxy, ethoxy, propoxy, butoxy, pentyloxy, isopropoxy, isobutoxy, isoamyloxy, cyclopropyloxy, cyclopentyloxy and cyclohexyloxy groups.

Representative examples of the phenol and phenol derivatives represented by the formula (6) include those set forth in Table 2.

TABLE 2

| Compound | $R^{62}$ | $R^{63}$ | $R^{64}$ | $R^{65}$ | $R^{66}$ |
|---|---|---|---|---|---|
| Phenol | H | H | H | H | H |
| Catechol | OH | H | H | H | H |
| Resorcinol | H | OH | H | H | H |
| Phloroglucinol | H | OH | H | OH | H |
| Pyrogallol | OH | OH | H | H | H |
| Orcinol | H | OH | H | Me | H |
| p-Ethylphenol | H | H | Et | H | H |
| o-Cresol | Me | H | H | H | H |
| m-Cresol | H | Me | H | H | H |
| 2,5-Dimethylphenol | Me | H | H | Me | H |
| 3,5-Dimethylphenol | H | Me | H | Me | H |
| Thymol | H | Me | H | H | i-Pr |
| Carvacrol | Me | H | H | i-Pr | H |
| o-Cyclohexylphenol | Cy | H | H | H | H |
| o-Hydroxydiphenyl | Ph | H | H | H | H |
| 2-Chloro-5-hydroxytoluene | H | Me | Cl | H | H |
| o-Chlorophenol | Cl | H | H | H | H |
| p-Chlorophenol | H | H | Cl | H | H |
| 2,4-Dichlorophenol | Cl | H | Cl | H | H |
| 2,4,6-Trichlorophenol | Cl | H | Cl | H | Cl |
| p-Bromophenol | H | H | Br | H | H |
| 2,6-Dibromophenol | Br | H | H | H | Br |
| 2,4,6-Tribromophenol | Br | H | Br | H | Br |
| Guaiacol | OMe | H | H | H | H |
| 3-Methoxyphenol | H | OMe | H | H | H |
| 4-Methoxyphenol | H | H | OMe | H | H |
| 2-Benzylphenol | Bz | H | H | H | H |
| 2-Phenyl-6-chlorophenol | Ph | H | H | H | Cl |

Representative examples of the naphthol and naphthol derivatives represented by the formula (7) include those set forth in Table 3.

TABLE 3

| Compound | $R^{71}$ | $R^{72}$ | $R^{73}$ | $R^{74}$ | $R^{75}$ | $R^{76}$ | $R^{77}$ | $R^{78}$ |
|---|---|---|---|---|---|---|---|---|
| 1-Naphthol | OH | H | H | H | H | H | H | H |
| 2-Naphthol | H | OH | H | H | H | H | H | H |
| 1,5-Dihydroxynaphthalene | OH | H | H | H | OH | H | H | H |
| 1,6-Dihydroxynaphthalene | OH | H | H | H | H | OH | H | H |
| 1,7-Dihydroxynaphthalene | OH | H | H | H | H | H | OH | H |
| 1,8-Dihydroxynaphthalene | OH | H | H | H | H | H | H | OH |
| 2,6-Dihydroxynaphthalene | H | OH | H | H | H | OH | H | H |
| 6-Methyl-1,7-dihydroxynaphthalene | OH | H | H | H | H | Me | OH | H |
| 4-Methoxy-1-naphthol | OH | H | H | OMe | H | H | H | H |
| 2-Chloro-1-naphthol | OH | Cl | H | H | H | H | H | H |
| 2,6-Dibromo-1,5- | OH | Br | H | H | OH | Br | H | H |

TABLE 3-continued

| Compound | $R^{71}$ | $R^{72}$ | $R^{73}$ | $R^{74}$ | $R^{75}$ | $R^{76}$ | $R^{77}$ | $R^{78}$ |
|---|---|---|---|---|---|---|---|---|
| dihyroxynaphthalene | | | | | | | | |
| 5-Nitro-1-naphthol | OH | H | H | H | $NO_2$ | H | H | H |

Remarks: H, OH, Me, OMe, Cl and Br have the same meaning as in Table 2, and $NO_2$ means nitro group.

Among these compounds, the naphthol derivatives are preferred, and 1,7-dihydroxynaphthalene and 4-methoxy-1-naphthol are particularly preferred.

Peroxidase can be a peroxidase of plant or animal origin (EC 1.11.1.7) as disclosed in U.S. Pat. Nos. 3,983,005 and 4,211,845, GB 2 036 963A, and others, or a peroxidase of microorganism origin (EC 1.11.1.7) as disclosed in Japanese Patent Provisional Publication No. 57(1982)-99192 and others. The peroxidase can be employed alone or in combination.

Examples of the peroxidase of plant origin include peroxidases extracted from horseradish, potato, fig tree sap, turnip, and Japanese radish. Examples of th peroxidase of animal origin include lacto-peroxidase extracted from milk and verdoperoxidase extracted from white corpuscle. Examples of the peroxidase of microorganism origin include peroxidase originating from microorganisms capable of producing non-specific peroxidase belonging to Genus Alternaria, Genus Cochliobolus, Genus Curvularia, or Genus Pellicularia.

Alternatively, inorganic compounds having peroxidase activity such as ferrous thiocyanate, ferrous tannate, ferrous ferrocyanide, potassium chromic sulfate, sodium iodide, potassium iodide, ammonium molybdate, and potassium molybdate as disclosed in U.S. Pat. Nos. 3,983,005 and 4,211,845 and GB No. 2 036 963A can be employed.

Among these peroxidases and other compounds having the peroxidase activity, peroxidases of plant origin and non-specific peroxidases of microorganism origin are preferred.

As described hereinbefore, the reagent layer comprised in the multilayer analytical element of the present invention is a reagent layer which comprises a combination of chromogen and coupler (a color indicator composition) and peroxidase dispersed or dissolved in a hydrophilic polymer binder.

There is no specific limitation on a hydrophilic polymer employable as the polymer binder, so far as the polymer is capable of forming a film and is substantially inert to peroxidase and the combination of chromogen and coupler. Examples of the hydrophilic polymer include gelatin, acid-processed gelatin, deionized gelatin, gelatin derivatives such as acylated gelatin, poly(vinyl alcohol), poly(vinylpyrrolidone), poly(sodium vinylbenzenesulfonate), carboxymethyl cellulose, sodium carboxymethylcellulose, hydroxyethylcellulose, methylcellulose, pullulan, pullulan derivatives, polyacrylamide, and acrylamide copolymers such as acrylamide-N-vinylpyrrolidone copolymer and acrylamide-2-hydroxyethylacrylamide copolymer. The thickness (dry basis) of the reagent layer generally ranges from approx. 5 $\mu m$ to approx. 100 $\mu m$, preferably from approx. 10 $\mu m$ to approx. 50 $\mu m$.

The peroxidase contained in the reagent layer generally amounts to from approx. 5,000 $U/m^2$ to approx. 100,000 $U/m^2$, preferably from approx. 10,000 $U/m^2$ to approx. 60,000 $U/m^2$, The combination of chromogen and coupler is necessarily incorporated in an amount equivalent to or more than the amount stoichiometrically corresponding to a presumed maximum amount of the analyte contained in the liquid sample under analysis. The amount of the combination of chromogen and coupler can be determined by those skilled in the art through experimental trials.

If the analyte is not hydrogen peroxide, but is able to produce hydrogen peroxide by a chemical reaction, an oxidase serving as a catalyst for the reaction between the analyte and oxygen for producing hydrogen peroxide can be included in the reagent layer or another layer. The oxidase included in the multilayer analytical element is necessarily chosen according to nature of the analyte. The oxidase can be employed singly, but a plurality of enzymes (containing at least one oxidase) can be employed for causing a series of continuous reactions. If required, a cofactor or an activator to oxidase and/or its coenzyme can be employed in conjunction with the oxidase.

The oxidase, if required, together with its coenzyme, can be included in a reagent layer containing the combination of chromogen and coupler, and peroxidase, or in a layer provided over the reagent layer. Otherwise, it can be included in both the reagent layer containing either of the combination of chromogen and coupler, and peroxidase, and one or more layers provided over the reagent layer. Thus, it can be included in two or more layers. The above-mentioned term "a layer provided over the reagent layer" means to include a porous spreading layer.

A reaction of a substrate catalyzed by oxidase requires oxygen. In this respect, since oxygen in a circumferential air is to be introduced from a porous spreading layer to diffuse into other layers, a multilayer analytical element in which an oxidase is included in a layer provided over the reagent layer containing the combination of chromogen and coupler, and peroxidase particularly in a porous spreading layer or a layar adjacent to the spreading layer so as to accomplish efficient diffusion of oxygen into the layers, as disclosed in GB No. 2 104 215A, is preferably employed for facilitating efficient progress of the oxidation reaction catalyzed by oxidase. In the case that the analyte is a hydrophobic substance such as a cholesterol ester, the analyte difficulty permeates the layer having a hydrophilic polymer binder. For this reason, oxidase is preferably included inside of a porous spreading layer in such a case.

The oxidase to be contained in a multilayer analytical element of the present invention may be an oxidase utilizing oxygen ($O_2$) as acceptor. Examples of the oxidase utilizing oxygen ($O_2$) as acceptor include the following enzymes: the number included in parenthesis given to the listed enzyme meaning EC number: glycollate oxidase (1.1.3.1), malate oxidase (1.1.3.3), glucose oxidase (1.1.3.4), hexose oxidase (1.1.3.5), cholesterol oxidase (1.1.3.6), aryl-alcohol oxidase (1.1.3.7), L-gulonolactone oxidase (1.1.3.8), galactose oxidase (1.1.3.9), alcohol oxidase (1.1.3.13), L-2-hydroxyacid oxidase (1.1.3.15), aldehyde oxidase (1.2.3.1), xanthine oxidase (1.2.3.2), pyruvate oxidase (1.2.3.3), pyruvate oxidase (CoA acetylating) (1.2.3.6), lathosterol oxidase (1.3.3.2), D-aspartate oxidase (1.4.3.1), L-aminoacid oxidase (1.4.3.2), D-aminoacid oxidase (1.4.3.3), amine oxidase (flavine-containing) (1.4.3.4), pyridoxaminephosphate oxidase (1.4.3.5), amine oxidase (copper-containing) (1.4.3.6), D-glutamate oxidase (1.4.3.7), sarcosine oxidase (1.5.3.1), N-methylaminoacid oxidase (1.5.3.2), $N^6$-methyl-L-lysine oxidase (1.5.3.4), uricase (ureate oxidase) (1.7.3.3), sulfite oxidase (1.8.3.1), ascorbate oxidase (1.10.3.3), 3-hydroxyanthranylate oxidase (1.10.3.5), arginine 2-monooxygenase (1.13.12.1), lysine 2-monooxigenase (1.13.12.2), tryptophan 2-monooxygenase (1.13.12.3), lactate oxidase (lactate 2-monooxygenase) (1.13.12.4), dimethylaniline monooxygenase (1.14.13.8), cholesterol 7$\alpha$-monooxygenase (1.14.13.17), flavoprotein-linked monooxygenase (1.14.14.1), phenylalanine monooxygenase (1.14.16.1), glycerol oxidase (available from Toyo Jozo Co., Ltd., Japan), and glycine oxidase (described in ENCYCLOPAEDIA CHIMICA, Vol. 3, published in September of 1960 by Kyoritsu Shppan Co., Ltd., Japan).

Examples of a combination of a plurality of enzymes including oxidase include the following:

a combination of glycerol kinase (2.7.1.30) and L-$\alpha$-glycerophosphate oxidase (1.1.99.5; or disclosed in U.S. Pat. No. 4,166,005, GB No. 1 585 909, GB No. 1 590 738, and FR No. 2 362 396), as disclosed in GB No. 1 590 738 and FR No. 2 362 396;

a combination of lipase having triglyceride-hydrolyzing activity, glycerol kinase (2.7.1.30), and L-$\alpha$-glycerophosphate oxidase (1.1.99.5; or disclosed in U.S. Pat. No. 4,166,005, GB No. 1 585 909, GB No. 1 590 738, and FR No. 2 362 396), as disclosed in GB No. 1 590 738 and FR No. 2 362 396;

a combination of lipase having esterase activity, protease, and cholesterol oxidase (1.1.3.6), as disclosed in U.S. Pat. No. 3,983,005;

a combination of glutamic-pyruvic transaminase (same as alanine aminotranspherase; 2.6.1.2) and pyruvate oxidase (1.2.3.3), as disclosed in DE No. 3 222 707 A1; and, a combination of glutamic-oxaloacetic transaminase (2.6.1.1), oxaloacetate decarboxylase (4.1.1.3), and pyruvate oxidase (1.2.3.3.), as disclosed in DE No. 3 222 707 A1.

Among these oxidases, preferably employable in the multilayer analytical element of the present invention are glucose oxidase, cholesterol oxidase, pyruvate oxidase, uricase, ascorbate oxidase, lactate oxidase, and glycerol oxidase. Also preferred are several combinations including the oxidase exemplified above.

The amount of oxidase to be contained in the multilayer analytical element can be determined principally by a ratio between a presumed maximum amount of a hydrogen peroxide-producible analyte contained in a liquid sample under analysis and activity values of oxidase and peroxidase. Thus, the amount of oxidase can be determined experimentally by those skilled in the art. The amount of oxidase generally ranges from approx. 1,000 U/m$^2$ to approx. 100,000 U/m$^2$, and preferably ranges from approx. 3,000 U/m$^2$ to approx. 50,000 U/m$^2$. In the case that oxidase is glucose oxidase, the amount generally ranges from approx. 2,000 U/m$^2$ to approx. 40,000 U/m$^2$, and preferably ranges from approx. 4,000 U/m$^2$ to approx. 20,000 U/m$^2$.

Each of peroxidase and oxidase has an optimum pH range respectively where their activities are kept at the maximum value. Their activities are also influenced by an ionic strength and natures of anions and cations present in the vicinity of these enzymes. Accordingly, it is very important for obtaining results satisfactory in the quantitative accuracy, reproducibility, etc. that a multilayer analytical element is so prepared that primarily a pH value of a reagent layer containing peroxidase, a reagent layer containing oxidase, or a reagent layer containing both of peroxidase and oxidase is adjusted to a respective optimum value, and that, if necessary, other factors such as the ionic strength and nature of coexisting ions are adjusted to show optimum conditions. For these reasons, it is especially advantageous that a multilayer analytical element of the present invention contains an acid, an alkali, a salt, a buffer reagent, a dissociating agent, a surface active agent, etc. in one or more of the functional layers such as a porous spreading layer, a reagent layer, and a light-shielding layer. The reagents and their amounts employed for the above-mentioned adjustment of the conditions vary depending upon the analytical purpose and other factors and can be selected in view of the analytical purpose.

In order to produce a detectable change in the presence of hydrogen peroxide by incorporating an acid, an alkali or a buffer reagent into the reagent layer containing the combination of chromogen and coupler, and peroxidase, the pH value is preferably adjusted to pH 7.0 of the optimum pH value for peroxidase or a value in the vicinity of pH 7.0, such as, in the range of pH 5.0 (approx.) to pH 9.0 (approx.), preferably pH 6.0 (approx.) to pH 8.0 (approx.).

Different oxidases have their optimum pH values: for instance, pH 5.6 (approx.) for glucose oxidase; pH 6.3 (approx.) for hexose oxidase; pH 5.8 (approx.) for cholesterol oxidase; pH 7.0 (approx.) for galactose oxidase; pH 7.5 (approx.) for alcohol oxidase; pH 7.5–8.5 for uricase; pH 5.6 (approx.) for ascorbate oxidase; and pH 7.5–7.7 for L-$\alpha$-glycerophosphate oxidase.

The layer containing oxidase is preferably adjusted to have an optimum pH value or a pH value in the vicinity of the optimum value, according to the requirement of nature of oxidase contained therein. Accordingly, an oxidase having an optimum pH value different from an optimum pH value of a peroxidase employed together is preferably included in a layer different from a peroxidase-containing layer. For instance, glucose oxidase can be included in a porous spreading layer or an adhesive layer (described hereinafter). In this case, said layer containing glucose oxidase can be so prepared to show under analytical procedures pH 5.6 of the optimum pH value for glucose oxidase or a value in the vicinity of pH 5.6, such as, in the range of pH 3.6 to pH 7.6, preferably pH 4.0 to pH 7.0, by incorporating appropriately an acid or a buffer thereinto.

Examples of the acid, alikali and buffer reagent employable for the pH adjustement of the reagent layer, other layers or the porous spreading layer include aliphatic hydroxycarboxylic acids (examples: glycolic acid, lactic acid, $\alpha$-hydroxybutyric acid, and citric acid, etc.), aliphatic dicarboxylic acids (examples: malonic acid, succinic acid, $\alpha$-methylglutaric acid, $\beta$-methylglutaric acid, 3,3-dimethylglutaric acid, and $\alpha,\alpha'$-dimethylglutaric acid, etc.), aliphatic monocarboxylic acids (examples: acetic acid, propionic acid, and butyric acid, etc.), lithium hydroxide, sodium hyroxide, potassium hydroxide, buffer reagents described in "Kagakubinran, Kiso-hen (Chemistry Handbook, fundamentals)" edited by the Chemical Society of Japan (Maruzen Tokyo, 1966), pp. 1312–1320 (examples: potassium hydrogen citrate-citric acid, and potassium dihydrogenphosphatepotassium hydrogenphosphate, etc.), and buffer reagents described in "Hydrogen Buffers for Biological Research" reported by Norman E. Goods, et al.: Biochemistry, 5(2), 467–477 (1966), "Data for Biochemical Research" Vol. 2 (Oxford at the Clarendon Press, 1966) pp. 476–508, Analytical Biochemistry, 104, 300–310 (1980), etc., (examples: 2-(N-morpholino)ethanesulfonic acid, sodium salt or potassium salt of N-2-hydroxyethylpiperazine-N'-2-hydroxypropane-3-sulfonic acid (Heppso), sodium salt or potassium salt of N-2-hydroxyethylpiperazine-N'-3-propanesulfonic acid (Epps), sodium salt or potassium salt of N-[tris(hydroxymethyl)-methyl]-3-aminopropanesulfonic acid (Taps), etc.), other buffer reagents (examples: sodium or potassium hydrogenmalate, and sodium or potassium monohydrogen-3,3-dimethylglutarate, etc.), and inorganic acids (examples: sulfuric acid, and phosphoric acid, etc.). Among these reagents, citric acid, tartaric acid, malic acid, glutaric acid, α-methylglutaric acid, β-methylglutaric acid, α,α'-dimethylglutaric acid and 3,3-dimethylglutaric acid, lithium hydroxide, Heppso Na salt or K salt, Epps Na salt or K salt, and Taps Na salt or K salt are preferred.

Into one or more layers selected from the group consisting of the reagent layers, other layers over the reagent layer, or the spreading layers, there can be incorporated a compound comprising a cation capable of forming in combination with $F^-$ ion a sparingly water-soluble salt having solubility of not more than 0.2 g. in 100 g. of water at 25° C. (sparingly soluble F salt-forming compound) as a preservative for eliminating interference (appearing as lowering of measured value, or scattering the measured value) due to NaF included in whole blood, plasma, and serum, as described in U.S. patent application Ser. No. 517,341 filed on July 26, 1983 in the name of Fuminori Arai, et al., and EPC application of Appln. No. 83107440.6. Examples of the cation include $Mg^{2+}$, $Ca^{2+}$, $Ba^{2+}$, etc. Examples of the counterpart anion include lower aliphatic monocarboxylate anions such as formate ion, acetate ion, and propionate ion; lower aliphatic dicarboxylate anions such as malonate ion, glutarate ion, and 3,3-dimethylglutarate ion; hydroxycarboxylate anions such as glycolate ion, lactate ion, malate ion, tartrate ion, citrate ion, and salicylate ion; halogen anions such as chloride ion and bromide ion; nitrate ion, phosphate ion, sulfate ion, thiosulfate ion, nitrite ion, sulfate ion, and azide anion ($N_3^-$). The amount of the sparingly soluble F salt-forming compound contained in the multilayer analytical element generally ranges from 0.1 meq. to 1 eq., preferably from 0.2 meq. to 0.5 eq. based on 1 $m^2$ of the element.

Into one or more layers selected from the group consisting of the reagent layer, other layers over the reagent layer, or the spreading layers, there can be incorporated a water-soluble monocarboxylic acid or a salt thereof having solubility of not less than 1 g. in 100 g. of water at 25° C. mainly for eliminating interference (appearing as lowering of measured value) due to catalase or substances having the catalase activity included in a blood, as described in U.S. patent application Ser. No. 530,207 filed on Sept. 8, 1983 in the name of Yoshikazu Amano, et al., and U.S. patent application Ser. No. 530,207, filed Sept. 8, 1983 in the name of Fuji Photo Film Co., Ltd. As the water-soluble monocarboxylic acids and salts thereof, there can be mentioned an aliphatic monocarboxylic acid or a salt thereof, an aromatic monocarboxylic acid or a salt thereof, and an aromatic group-substituted aliphatic monocarboxylic acid or a salt thereof. These water-soluble monocarboxylic acids can be employed singly or in combination.

The aliphatic monocarboxylic acid can be a straight or branched-chain saturated aliphatic monocarboxylic acid having 1–5 carbon atoms, such as formic acid, acetic acid, propionic acid, butyric acid, valeric acid, isobutyric acid or isovaleric acid. The salt of an aliphatic monocarboxylic acid can be an alkali metal salt of the straight or branched-chain saturated aliphatic monocarboxylic acid having 1–5 carbon atoms, such as a lithium salt, a sodium salt, or a potassium salt. Otherwise, an ammonium salt can be employed. Examples of the salt include a lithium salt, a sodium salt, a potassium salt and an ammonium salt of formic acid, acetic acid, propionic acid, butyric acid, valeric acid, isobutyric acid, and isovaleric acid.

Examples of the salt of an aromatic monocarboxylic acid include lithium benzoate, sodium benzoate, potassium benzoate, ammonium benzoate, sodium o-toluylate, sodium m-toluylate, sodium p-toluylate, and ammonium toluylate.

Examples of the aromatic group-substituted aliphatic monocarboxylic acid and the salt thereof include phenylacetic acid, sodium phenylacetate, potassium phenylacetate, and ammonium phenylacetate.

Among these water-soluble monocarboxylic acids and salts thereof, preferred are acetic acid, propionic acid, sodium formate, potassium formate, sodium acetate, potassium acetate, ammonium acetate, sodium propionate, potassium propionate, and ammonium propionate. The amount of the water-soluble monocarboxylic acid or the salt thereof contained in the multilayer analytical element generally ranges from 0.1 meq. to 1 eq., preferably from 0.2 meq. to 0.5 eq. based on 1 $m^2$ of the element.

The sparingly soluble F salt-forming compound and the water-soluble monocarboxylic acid or the salt thereof can be included in combination. Otherwise, compounds having both activities such as $(CH_3COO)_2Ca$, $(CH_3COO)_2Mg$, etc. can be employed.

The porous spreading layer (referred to herein as "spreading layer") of the multilayer analytical element of the present invention is arranged in the outmost position of the element. In other words, the spreading layer is provided on the outmost position far from the support via the reagent layer. The liquid sample is applied or spotted onto the spreading layer. The function of this layer is to supply a liquid sample together with an analyte contained therein into the reagent layer at an approximately constant volume per unit area regardless of its applied volume, that is to say, "metering effect". Thus, this layer acts as a spreader for a liquid sample. Because of such spreading action, a volume of the liquid sample supplied to the reagent layer per unit area is automatically adjusted to a certain value regardless of its applied volume. This means that a liquid sample can be analyzed quantitatively without precise measurement of the volume when applied to the multilayer analytical element. However, it should be understood that the use of the multilayer analytical element of the invention never excludes doing precise measurement of a liquid sample in carrying out a quantitative analysis procedure. The precise measurement of a liquid sample is sometimes advantageous to increase accuracy of the analysis.

Example of the porous spreading layer of the present invention include a non-fibrous isotropically porous layer as disclosed in Japanese Patent Provisional Publication (JPPP) No. 49(1974)-53888 (Japanese Patent Publication (Jap. Publn.) No. 53(1978)-21677), U.S. Pat. No. 3,992,158, and GB No. 1 440 464, for instance, a membrane filter, a blushed polymer layer, and an isotropically porous layer comprising voids defined by fine spheres or particles bound to each other through a polymer binder (adhesive); an isotropically porous layer having continuous voids and being formed by three-dimensional matrix in which fine spherical beads are bound in point-to-point contact in all directions through binder not swelling with water, as disclosed in U.S. Pat. No. 4,258,001; a fibrous anisotropically porous spreading layer consisting of water-washed fabrics or hydrophilically processed fabrics, as disclosed in U.S. Pat. No. 4,292,272; a fibrous anisotropocally porous spreading layer consisting of fabrics having phisically activated surfaces, as disclosed in GB No. 2 087 074A; and a fibrous anisotropic porous spreading layer consisting of paper, paper filter or no-woven fabrics containing synthetic polymer fiber pulps, as disclosed in GB No. 2 087 074A. Any of these spreading layers can be provided to the analytical element of the invention in manners disclosed in these patent specifications. Otherwise, a membrane filter or blushed polymer layer containing titanium dioxide, zinc oxide, or barium sulfate in the form of fine powder disclosed in U.S. Pat. No. 3,992,158 and GB No. 1 440 464 can be employed in the analytical element of the invention for serving as a spreading layer and also as a light-shielding layer (radiation-blocking layer, white background layer, or light-reflecting layer), details being given hereinafter. Further, a membrane filter or a blushed polymer layer containing carbon black can be employed as a spreading layer which also serves as a light-shielding layer, as described hereinafter. If a liquid sample is a whole blood, the spreading layer preferably is the aforementioned isotropically porous layer having continuous voids and being formed by three-dimensional matrix, or the fibrous anisotropically porous spreading layer.

The multilayer analytical element of the invention can be provided with a light-shielding layer (radiation-blocking layer, background layer, or light-reflecting layer) capable of allowing permeation of water and analyte, between the reagent layer and the spreading layer.

The light-shielding layer is advantageously provided if the analytical element is employed for analysis of a liquid sample containing colored particles such as the whole blood containing red corpuscles. In more detail, colored particles positioned on one side of the light-shielding layer are optically shielded by the light-shielding layer from observation through the transparent support. Accordingly, the colorimetric or fluorometric measurement is not interfered by the presence of colored particles. The light-shielding layer can be composed of a fine powder such as finely particulated titanium dioxide, barium sulfate, zinc oxide, aluminum or carbon black dispersed within a water- and analyte-permeable, hydrophilic polymer binder. The light-shielding layer has a thickness in the range of from 5 to 100 μm, preferably 5 to 30 μm, and allows a liquid component and an analyte of a sample solution passing therethrough. The polymer binder for the preparation of the light-shielding layer can be optionally selected from the hydrophilic polymers described hereinbefore in connection with the binder for the reagent layer.

The light-shielding layer can be a porous light-shielding layer consisting of membrane filter (blushed polymer layer) containing light-shielding particles such as finely particulated titanium dioxide, zinc oxide, barium sulfate and carbon black. The porous light-shielding layer can be provided to the analytical element in the manner disclosed in U.S. Pat. Nos. 3,992,158 and 4,166,093, and GB No. 1 440 464.

The multilayer analytical element of the present invention can be provided with an adhesive layer for superposing the spreading layer on the reagent layer, the light-shielding layer, or other optionally-placed layers under increased adhesion to form an integrally laminated structure. The adhesive layer is preferably provided if the spreading layer is made of a porous sheet, a porous film or a porous membrane.

The adhesive layer can be produced from one or more of the water- and analyte-permeable hydrophilic polymer described hereinbefore in connection with the binder for the reagent layer. The adhesion of the spreding layer to the adhesive layer can be carried out by placing a porous sheet, film or membrane under pressure on an adhesive layer consisting of half-dried hydrophilic polymer or wetted with water or an aqueous solution containing a surface active agent. The adhesive layer has a thickness in the range of from 0.5 to 15 μm, preferably 0.5 to 5 μm.

The multilayer analyteical element of the invention can be provided, if desired, with a variety of layers such as a barrier layer or a liquid-blocking layer disclosed in U.S. Pat. No. Re. 30,267, Japanese Patent Provisional Publication No. 58(1983)-77660 and GB No. 2 114 737A, etc.; a detection layer or a mordant layer disclsoed in U.S. Pat. Nos. 4,042,335 and 4,144,306, etc.; a migration inhibiting layer disclosed in U.S. Pat. No. 4,166,093; the intermediate layer disclosed in U.S. Pat. Nos. 4,098,574 and 4,042,335, etc.; a protein-permeable hydrophilic binder polymer layer disclosed in U.S. Pat. Nos. 4,144,306 and 4,268,563, GB No. 1 474 285, EP No. 0044775 A1, U.S. Pat. No. 4,333,733, Japanese Patent Application No. 57(1982)-61936, etc.; a reagent layer comprising hydrophobic particles in which a reagent is contained under dispersion in a hydrophilic binder disclosed in U.S. Pat. No. 4,356,149; a porous material (patch) for application and supply of a liquid sample in a certain limited area disclosed in DE No. 3 133 538 A1; and a porous layer having a certain limited area and containing a reagent such as enzyme disclosed in DE No. 3 222 707 A1.

The multilayer analytical element of the present invention comprises, in sequence, a spreading layer, a reagent layer containing peroxidase, and a transparent support.

Among arrangements of the various layers, preferred are:

an arrangement comprising, in sequence, a spreading layer, a light-shielding layer, a reagent layer containing peroxidase, and a transparent support;

an arrangement comprising, in sequence, a spreading layer, an adhesive layer, a light-shielding layer, a reagent layer containing peroxidase, and a transparent support;

an arrangement comprising, in sequence, a spreading layer, a light-shielding layer containing oxidase, a reagent layer containing peroxidase, and a transparent support;

an arrangement comprising, in sequence, a spreading layer, an adhesive layer containing oxidase, a light-shielding layer, a reagent layer containing peroxidase, and a transparent support;

an arrangement comprising, in sequence, a spreading layer containing oxidase, an adhesive layer containing oxidase, a light-shielding layer, a reagent layer containing peroxidase, and a transparent support;

an arrangement comprising, in sequence, a spreading layer, an adhesive layer containing oxidase, a light-shielding layer, a reagent layer containing peroxidase, and a transparent support;

an arrangement comprising, in sequence, a spreading layer, a light-shielding layer, a reagent layer containing both of peroxidase and oxidase, and a transparent support;

an arrangement comprising, in sequence, a spreading layer, an adhesive layer, a light-shielding layer containing oxidase, a reagent layer containing both of peroxidase and oxidase, and a transparent support;

an arrangement comprising, in sequence, a spreading layer, a reagent layer containing oxidase, a light-shielding layer, a reagent layer containing both of peroxidase and oxidase, and a transparent support; and other variations of the above-described arrangements.

The multilayer analytical element of the present invention can be prepared in the manners disclosed in the aforementioned patent specifications. Examples of the detailed procedures are described in the hereinafter-given working examples.

The multilayer analytical element of the invention can be employed in quantitative analysis of analytes contained in a variety of liquid samples in the same manners as disclosed in the aforementioned patent specifications. The analytical element of the invention is preferably received in a slide frame and employed in the form of an analytical slide as disclosed in Japanese Utility Model Provisional Publication No. 54(1979)-162294, U.S. Pat. Nos. 4,387,990 and 4,169,751, and Japanese Patent Provisional Publication No. 57(1982)-63452. Otherwise, the analyteical element of the invention is preferably provided with a liquid sample-spreading assistant material (or a sample-spreading assisting element) on the porous spreading layer to form an analytical slide as disclosed in Japanese Patent Provisional Publication No. 57(1982)-182648. The analytical element in the form of such a slide is preferred in all aspects, namely, preparation, transportation, storage, measurement procedure and so forth.

The present invention will be further described by the following examples, which are not given to restrict the invention.

EXAMPLE 1

A reagent layer for quantitative analysis of glucose concentration in blood, having a thickness of 15 μm (dry basis), was formed on a transparent polyethylene terephthalate (PET) film (thickness: 185 μm) having a gelatin subbing layer, by coating the following composition thereon.

Peroxidase: 25000 IU
1,7-Dihydroxynaphthalene: 5 g.
Compound (6): 18 g.
Gelatin: 200 g.
Nonion HS 210 (polyoxyethylenenonylphenyl ether: produced by Nippon Oils & Fats Co., Ltd., Japan): 2 g.
Water: 1800 ml.

On the reagent layer, a light-shielding layer having a thickness of 15 μm (dry basis) containing 8 g. of powdery titanium dioxide, 0.2 g. of Nonion HS 210 and 50,000 IU of glucose oxidase dispersed in 1 g. of gelatin was formed thereon by coating an aqueous coating dispersion.

On the light-shielding layer, an adhesive layer having a thickness of 4 μm (dry basis) was formed by coating thereon a coating mixture of 4 g. of gelatin and 0.2 g. of Nonion HS 210 in 100 ml. of water.

The adhesive layer was wetted with water in an amount of 30 g./m², and subsequently a cotton broadcloth (100% cotton, woven from cotton yarn of 100 count, manufactured by Toyobo Co., Ltd., Japan) was pressed onto the adhesive layer and dried to give a porous spreading layer. Thus, a multilayer analytical element for quantitative analysis of glucose was prepared.

The analytical element was cut to obtain a square tip (1.5 cm × 1.5 cm), which was in turn inserted into a plastic mount disclosed in U.S. patent application Ser. No. 308,205, filed Oct. 2, 1981 as well as Japanese Patent Provisional Publication (JPPP) No.57(1982)-63452, to prepare an analytical slide for quantitative analysis of glucose.

A human whole blood was collected in the presence of heparin. To portions of the human whole blood were added different amounts of glucose, to obtain three human whole blood samples (glucose contents are set forth in Table 4). The liquid sample in the amount of 6 μl. was spotted on the spreading layer of the analytical slide, which was then incubated at 37° C. for 6 min., and subjected to reflective photometry from the PET film side at wavelength of 500 nm. The results are set forth in Table 4, and further illustrated in the form of a calibration curve in FIG. 1.

COMPARISON EXAMPLE 1

An analytical slide for quantitative analysis of glucose was prepared in the same manner as in Example 1 except that the compound (6) in the composition for the preparation of the reagent layer was replaced with 18 g. of the compound ($C_1$) (i.e. 4-aminoantipyrine). The results are set forth in Table 4, and further illustrated in the form of a calibration curve in FIG. 1.

TABLE 4

| | Glucose Concentration in Human Whole Blood* (mg/dl) | | | |
|---|---|---|---|---|
| | 100 | 250 | 415 | 561 |
| Example 1 (According to the invention) | 0.44 | 0.68 | 0.90 | 1.05 |
| Comparison Example 1 (Control) | 0.38 | 0.59 | 0.79 | 0.94 |

Remark*: value obtained upon separating plasma from the human whole blood sample containing glucose by centrifuge and determining the glucose concentration in the plasma through Hexokinase-G-6-PDH method.

The results given in Table 4 and FIG. 1 indicate that the analytical slide employing the multilayer analytical element for quantitative analysis of glucose according to the invention is superior to the control analytical slide of the comparison example 1 in the optical density of color formed thereon in the glucose analysis as well as in the steepness of slope (γ). This means that the analytical slide employing the multilayer element of the invention is highly sensitive. Moreover, the steepness of slope (γ) is maintained at a high level up to the region where the glucose concentration is high. These results accordingly indicate that the multilayer analytical element of the invention is broadened in the measurable range and further improved in the measurement accuracy.

EXAMPLE 2

A reagent layer for quantitative analysis of glucose concentration in blood, having a thickness of 15 μm (dry basis), was formed on a transparent PET film (thickness: 185 μm) having a gelatin subbing layer, by coating the following composition thereon.

Peroxidase: 25000 IU
Glucose oxidase: 40000 IU
1,7-dihydroxynaphthalene: 5 g.
Compound (6), monohydrochloride: 20 g.
Gelatin: 200 g.
Nonion HS 210: 2 g.
Water: 1800 ml.

On the reagent layer, a light-shielding layer having a thickness of 15 μm (dry basis) containing 8 g. of powdery titanium dioxide and 0.2 g. of Nonion HS 210 dispersed in 1 g. of gelatin was formed thereon by coating an aqueous coating dispersion.

On the light-shielding layer, an adhesive layer having a thickness of 4 μm (dry basis) was formed by coating thereon a coating mixture of 4 g. of gelatin and 0.5 g. of Nonion HS 210 in 100 ml. of water.

The adhesive layer was wetted with water in an amount of 30 g./m², and subsequently a cotton broadcloth (100% cotton, woven from cotton yarn of 100 count, manufactured by Toyobo Co., Ltd., Japan) was pressed onto the adhesive layer and dried to give a porous spreading layer. Thus, a multilayer analytical element for quantitative analysis of glucose was prepared.

The analytical element was cut to obtain a square tip (1.5 cm × 1.5 cm), which was in turn inserted into a plastic mount disclosed in U.S. patent application Ser. No. 308,205, filed Oct. 2, 1981 as well as Japanese Patent Provisional Publication (JPPP) No.57(1982)-63452, to prepare an analytical slide for quantitative analysis of glucose.

A human whole blood was collected in the presence of heparin. To portions of the human whole blood were added different amounts of glucose, to obtain three human whole blood samples (glucose contents are set forth in Table 5). The liquid sample in the amount of 6 μl. was spotted on the spreading layer of the analytical slide, which was then incubated at 37° C. for 6 min., and subjected to reflective spectroscopy from the PET film side at wavelength of 500 nm. The results are set forth in Table 5, and further illustrated in the form of a calibration curve in FIG. 2.

COMPARISON EXAMPLE 2

An analytical slide for quantitative analysis of glucose was prepared in the same manner as in Example 1 except that the monohydrochloride of the compound (6) in the composition for the preparation of the reagent layer was replaced with 20 g. of monohydrochloride of the compound ($C_1$). The results are set forth in Table 5, and further illustrated in the form of a calibration curve in FIG. 2.

TABLE 5

| | Glucose Concentration in Human Whole Blood* (mg/dl) | | | |
|---|---|---|---|---|
| | 92 | 210 | 405 | 580 |
| Example 2 (According to the invention) | 0.41 | 0.65 | 0.87 | 0.97 |
| Comparison Example 2 (Control) | 0.35 | 0.50 | 0.72 | 0.78 |

Remark*: value obtained in the same manner as described in the remark given to Table 4.

Figure 2:
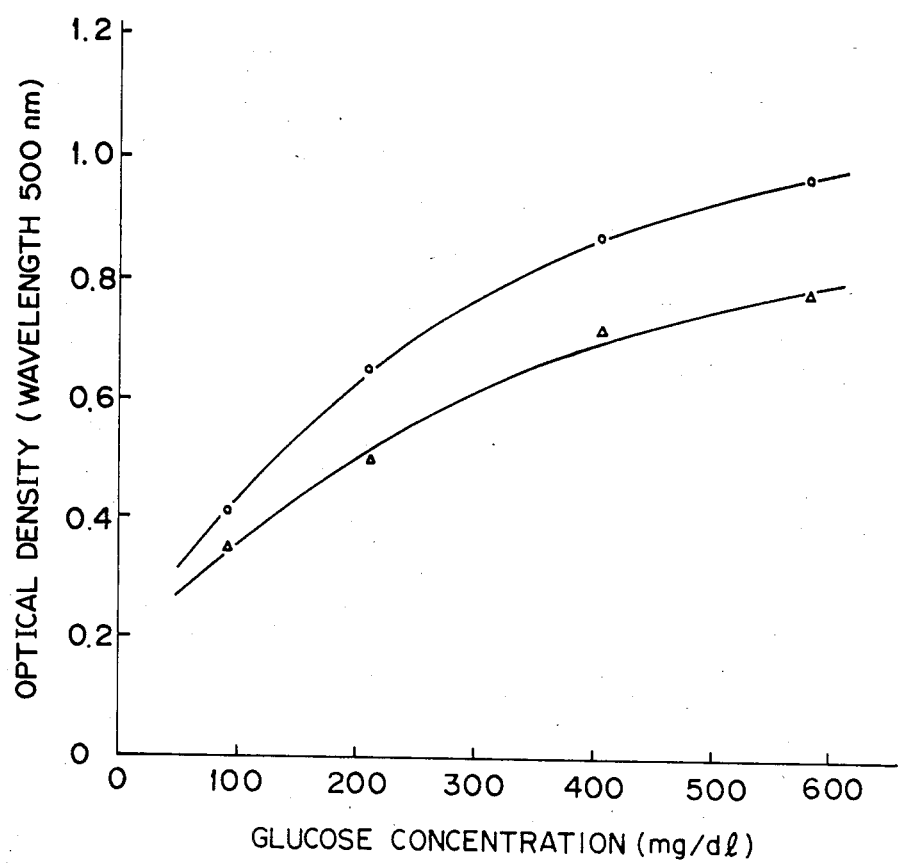

The results given in Table 5 and FIG. 2 indicate that the analytical slide employing the multilayer analytical element for quantitative analysis of glucose according to the invention is superior to the control analytical slide of the comparison example 2 in the optical density of color formed thereon in the glucose analysis as well as in the steepness of slope (γ). This means that the analytical slide employing the element of the invention is highly sensitive. Moreover, the steepness of slope (γ) is maintained at a high level up to the region where the glucose concentration is high. These results accordingly indicate that the multilayer analytical element of the invention is broadened in the measurable range and further improved in the measurement accuracy.

EXAMPLE 3

Four analytical slides for quantitative analysis of glucose were prepared in the same manner as in Example 2 except that the monohydrochloride of the compound (6) was replaced with 18 g. of the compounds (1), (6), (7), and (18), respectively.

COMPARISON EXAMPLE 3

An analytical slide for quantitative analysis of glucose was prepared in the same manner as in Example 2 except that the monohydrochloride of the compound (6) was replaced with 18 g. of the compound ($C_2$) (i.e. 4-amino-1,1-dimethyl-3-phenyl-3-pyrazolin-5-one).

Relative Sensitivity of Analytical Slide (Multilayer Analytical Element)

On each of the six analytical slides (four slides prepared in Example 3, and two slides prepared in Comparison Examples 2 and 3) were spotted 6 μl. of a glucose-incorporated human whole blood (glucose concentration: 100 mg./dl., determined on separated plasma through the Hexokinase-G-6-DPH method) and distilled water, respectively. The analytical slide was then incubated at 37° C. for 6 min., and subjected to reflective spectroscopy from the PET film side at 500 nm.

Based on the observed optical density (OD) values, the relative sensitivity of the analytical slide (multilayer analytical element) was calculated according to the following equation:

Relative Sensitivity = [OD (slide n: human whole blood) − OD (slide n: distilled water)]/[OD (slide 5: human whole blood) − OD (slide 5: distilled water)]

in which OD (slide n: human whole blood) means an optical density value determined on the above-mentioned human whole blood using the analytical slide n (n is one of numbers of 1 to 6, and was allotted to each of the six analytical slides as in set forth in Table 6). Others are expressed in the same manner.

Solubility in Cold Water

The solubility in 10 ml. of cold water (distilled water at 25° C.) was determined on the compounds (1), (6), (7), (18), ($C_1$) and ($C_2$), respectively. The results were classified into three levels, namely, an amount of more than 10 g. is soluble; an amount of not more than 5 g. but not less than 0.2 g. is soluble; and an amount of not more than 0.2 g. is soluble. The results are set forth in Table 6.

Relative Sensitivity in Aqueous Solution System

The following color-forming composition solutions were prepared using, as coupler, 1,7-dihydroxynaphthalene and, as chromogen, the compounds (1), (6), (7), (18), ($C_1$) and ($C_2$), respectively.

Chromogen: 10 μmol
1,7-Dihydroxynaphthalene: 50 μmol
Peroxidase: 50 IU
Phosphate buffer: added to adjust to pH 6.0

The color-forming solution having the above composition (5 ml.) was incubated at 37° C. for 3 min., and subsequently 50 μl. of aqueous $H_2O_2$ solution (four levels from 1 mmol to 6 mmol and blank, respectively) was dropped into the incubated color-forming solution. The solution was further incubated at 37° C. for 10 min., and immediately subjected to transmissive spectroscopy at the wavelength of 515 nm for measurement of optical density of the formed color. The relationships between the $H_2O_2$ concentrations and the measured optical density values on the formed color (the value was calculated by subtracting an optical density of the color formed in the blank solution from an optical density of the color formed in the aqueous $H_2O_2$ incorporated solution) were plotted on an orthgonal axes graph to determine the steepness of slope of the calibration curve. The relative sensitivity of each compound is set forth in Table 6 in terms of a relative steepness value based on the the reference steepness obtained in the measurement on the solution using the compound ($C_1$). In Table 6, the reference steepness is given as 1.0.

TABLE 6

| Anal. Slide | Compound No. | Relative Sensitivity (Slide) | Solubility in Water | Relative Sensitivity (aq. sol.) |
|---|---|---|---|---|
| Example for the invention ||||| 
| 1 | (1) | 1.4 | B | 0.99 |
| 2 | (6) | 1.9 | A | 0.70 |
| 3 | (7) | 2.0 | A | 0.65 |
| 4 | (18) | 1.9 | A | 0.82 |
| Example for comparison ||||| 
| 5 | ($C_1$) | 1.0 | C | 1.0 |
| 6 | ($C_2$) | 1.0 | C | 0.77 |

Remark
A: solubility in 10 ml. of cold water is not more than 0.2 g;
B: solubility in 10 ml. of cold water is more than 0.2 g. and not more than 5 g.;
C: solubility in 10 ml. of cold water is equal to or more than 10 g.

The results set forth in Table 6 clearly indicate that the compounds employed in the examples for the present invention are prominently high in the sensitivity within the analytical slide (multilayer analytical element) as compared with the compounds employed for comparison, though the former compounds for the invention are almost low in the sensitivity in the aqueous solution measurement system and are apparently low in the solubility in the cold water, as compared with the latter compounds for comparison.

EXAMPLE 4

A reagent layer for quantitative analysis of glucose concentration in blood, having a thickness of 15 μm (dry basis), was formed on a transparent PET film (thickness: 185 μm) having a gelatin subbing layer, by coating the following composition thereon.

Peroxidase: 25000 IU
1,7-Dihydroxynaphthalene: 5 g.
Compound (6): 18 g.
Gelatin: 200 g.
Nonion HS 210: 2 g.
Water: 1800 ml.

On the reagent layer, a light-shielding layer having a thickness of 15 μm (dry basis) containing 8 g. of powdery titanium dioxide, 0.2 g. of Nonion HS 210 and 50,000 IU of glucose oxidase dispersed in 1 g. of gelatin was formed by coating an aqueous coating dispersion.

On the light-shielding layer, an adhesive layer having a thickness of 4 μm (dry basis) was formed by coating thereon a coating mixture of 4 g. of gelatin, 0.5 g. of 3,3-dimethylglutaric acid and 0.5 g. of Nonion HS 210 in 100 ml. of water.

The adhesive layer was wetted with water in an amount of 30 g./m², and subsequently a cotton broadcloth (100% cotton, woven from cotton yarn of 100 count, manufactured by Toyobo Co., Ltd., Japan) was pressed onto the adhesive layer and dried to give a porous spreading layer. Thus, a multilayer analytical element for quantitative analysis of glucose was prepared.

The analytical element was cut to obtain a square tip (1.5 cm × 1.5 cm), which was in turn inserted into a plastic mount disclosed in U.S. Patent Application Ser. No. 308,205, filed Oct. 2, 1981 as well as Japanese Patent Provisional Publication (JPPP) No.57(1982)-63452, to prepare an analytical slide for quantitative analysis of glucose.

To human plasmas were added different amounts of glucose, to obtain three human plasma samples (glucose contents are set forth in Table 7) for measurement. The simple human plasma to which was added no glucose was also employed for measurement. The liquid sample in the amount of 6 μl. was spotted on the spreading layer of the analytical slide, which was then incubated at 37° C. for 6 min., and subjected to reflective photometry from the PET film side at 500 nm. The results are set forth in Table 7, and further illustrated in the form of a calibration curve in FIG. 3.

COMPARISON EXAMPLE 4

An analytical slide for quantitative analysis of glucose was prepared in the same manner as in Example 4 except that the compound (6) was replaced with 18 g. of the compound ($C_1$). The results are set forth in Table 7, and further illustrated in the form of a calibration curve in FIG. 3.

TABLE 7

| | Glucose Concentration in Human Whole Blood* (mg/dl) | | | |
|---|---|---|---|---|
| | 100 | 250 | 351 | 425 |
| Example 4 (According to the invention) | 0.60 | 1.15 | 1.42 | 1.59 |
| Comparison Example 4 | 0.57 | 1.04 | 1.27 | 1.41 |

TABLE 7-continued

| Glucose Concentration in Human Whole Blood* (mg/dl) | | | |
|---|---|---|---|
| 100 | 250 | 351 | 425 |
| (Control) | | | |

Remark*: value obtained in the same manner as described in the remark given to Table 4.

Figure 3:
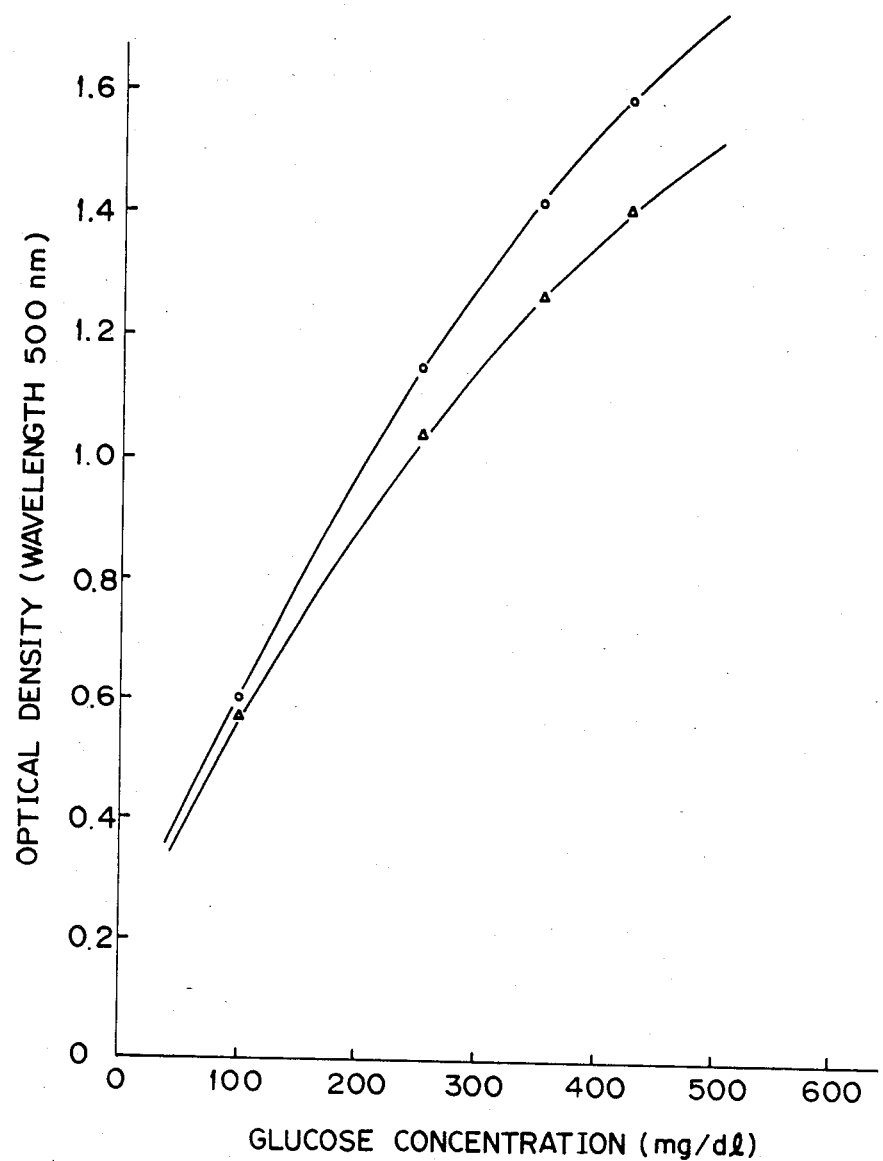

The results given in Table 7 and FIG. 3 indicate that the analytical slide employing the multilayer analytical element for quantitative analysis of glucose according to the invention which has the adhesive layer being adjusted to a low pH level by addition of the weak acid, 3,3-dimethylglutaric acid, whereby the reagent layer is maintained at a low pH level in practical use, is superior to the control analytical slide of the comparison example 4 (which is also maintained at a low pH level in practical use) in the optical density of color formed thereon in the glucose analysis as well as in the steepness of slope ($\gamma$). This means that the analytical slide employing the element of the invention is highly sensitive. Moreover, the steepness of slope ($\gamma$) is maintained at a high level up to the region where the glocose concentration is high. These results accordingly indicate that the multilayer analytical element of the invention is broadened in the measurable range and further improved in the measurement accuracy.

EXAMPLE 5

An analytical slide for quantitative analysis of glucose was prepared in the same manner as in Example 4 except that the compound (6) was replaced with 18 g. of the compound (18).

The analytical procedure was repeated in the same manner as in Example 4, showing in almost the same result as in Example 4.

EXAMPLE 6

An analytical slide for cholesterol analysis was prepared in the same manner as in Example 1 except that the light-shielding layer was formed to have the following composition, and the adhesive layer was formed by the use of the following coating solution.

Composition of Light-shielding Layer

Powdery titanium dioxide: 8 g.
Gelatin: 1 g.
Cholesterol oxidase: 50000 IU
Nonion HS 210: 0.2 g.

Composition of Adhesive Layer Coating Solution

Gelatin: 4 g.
Sodium acetate: 2 g.
Cholesterol esterase: 25000 IU
Nonion HS 210: 0.2 g.
Water: 100 ml.

The above analytical slide was subjected to the color formation test stated below, using a non-hemolytic human serum and a partially hemolytic human serum respectively containing free cholesterol and ester-type cholesterol in the amount of 375 mg./dl. (calculated in terms of free cholesterol amount). The serum sample in the amount of 10 $\mu$l. was spotted on the spreading layer of the analytical slide, which was then incubated at 37° C. for 6 min., and subjected to reflective photometry from the PET film side at 500 nm. The optical density values were 0.53 and 0.51, respectively.

COMPARISON EXAMPLE 5

An analytical slide for cholesterol analysis was prepared in the same manner as in Example 6 except that the reagent layer was formed to have the following composition.

Composition of Reagent Layer

Peroxidase: 25000 IU
1,7-Dihydroxynaphthalene: 5 g.
Compound ($C_1$): 18 g.
Gelatin: 200 g.
Nonion HS 210: 2 g.

The above analytical slide was subjected to the color formation test described in Example 6 using the same sample as in Example 6. The color formed upon incubation at 37° C. for 6 min., and was measured by reflective photometry at 500 nm. The optical density values were 0.48 for the non-hemolytic serum, and 0.46 for the partially hemolytic serum.

We claim:

1. In a multilayer analytical element having a water-impermeable, light-transmissive support, a reagent layer containing a color forming reagent composition for detection of hydrogen peroxide including at least a combination of a chromogen and a coupler, and peroxidase, which produces a detectable change in the presence of peroxidase and hydrogen peroxide, and a porous spreading layer, which are superposed in this order, the improvement which comprises said chromogen being a 1,2,3,-tri-substituted compound of 4-amino-3-pyrazolin-5-one having a solubility in water at 25° C. lower than that of 4-amino-2,3-dimethyl-1-phenyl-3-pyrazolin-5-one.

2. The multilayer analytical element as claimed in claim 1, in which said coupler is a compound capable of forming a dye together with the 1,2,3-tri-substituted compound of 4-amino-3-pyrazolin-5-one through oxidative coupling reaction in the presence of peroxidase and hydrogen peroxide.

3. The multilayer analytical element as claimed in claim 1 or 2, in which said reagent layer contains said 1,2,3-tri-substituted compound of 4-amino-3-pyrazolin-5-one, said coupler and peroxidase.

4. The multilayer analytical element as claimed in claim 1 or 2, in which oxidase is contained in said reagent layer or any other layer.

5. The multilayer analytical element as claimed in claim 4, in which said oxidase is selected from the group consisting of glucose oxidase, cholesterol oxidase, pyruvate oxidase, uricase, ascorbate oxidase, lactate oxidase, and glycerol oxidase.

6. The multilayer analytical element as claimed in claim 4, in which said oxidase is glucose oxidase.

7. The multilayer analytical element as claimed in claim 4, in which said oxidase is cholesterol oxidase.

* * * * *